(12) United States Patent
Lo et al.

(10) Patent No.: US 10,476,257 B2
(45) Date of Patent: Nov. 12, 2019

(54) INTERFACE CONTROL CIRCUIT AND CONTROL METHOD THEREOF

(71) Applicant: RICHTEK TECHNOLOGY CORPORATION, Zhubei, HsinChu (TW)

(72) Inventors: Chieh-Min Lo, Miaoli (TW); Yi-Syue Jhu, New Taipei (TW)

(73) Assignee: RICHTEK TECHNOLOGY CORPORATION, Zhubei, Hsinchu (TW)

( * ) Notice: Subject to any disclaimer, the term of this patent is extended or adjusted under 35 U.S.C. 154(b) by 314 days.

(21) Appl. No.: 15/639,656

(22) Filed: Jun. 30, 2017

(65) Prior Publication Data
US 2018/0269676 A1    Sep. 20, 2018

(30) Foreign Application Priority Data
Mar. 17, 2017  (CN) .......................... 2017 1 0160096

(51) Int. Cl.
| | |
|---|---|
| *H02H 5/00* | (2006.01) |
| *H02H 5/08* | (2006.01) |
| *G01N 27/22* | (2006.01) |
| *H01R 13/66* | (2006.01) |
| *H01R 24/60* | (2011.01) |
| *H01R 107/00* | (2006.01) |

(52) U.S. Cl.
CPC ........... *H02H 5/083* (2013.01); *G01N 27/226* (2013.01); *H01R 13/6683* (2013.01); *H01R 24/60* (2013.01); *H01R 2107/00* (2013.01); *H01R 2201/20* (2013.01)

(58) Field of Classification Search
None
See application file for complete search history.

(56) References Cited

U.S. PATENT DOCUMENTS

| | | | |
|---|---|---|---|
| 8,009,400 B2 * | 8/2011 | Chao ...................... | H02H 9/004 361/56 |
| 8,773,271 B1 * | 7/2014 | Stevens .................. | H03K 17/94 340/604 |
| 9,577,389 B2 * | 2/2017 | Dicks ................. | H01R 13/6683 |

* cited by examiner

*Primary Examiner* — Stephen W Jackson
(74) *Attorney, Agent, or Firm* — Tung & Associates

(57) ABSTRACT

An interface control circuit comprises an interface signal transceiver circuit coupled with an interface which includes at least one interface pin for transmitting and/or receiving an interface signal through the interface, and a protection circuit for generating a protection control signal according to a capacitance of a first interface pin. During a predetermined detection time period starting from an attaching event, the protection circuit senses the capacitance of the first interface pin, and determines that there is an electrolytic substance existing and coupled with the first interface pin when the capacitance is larger than a predetermined first capacitance threshold. The protection control signal triggers the interface signal transceiver circuit to execute a protection operation. The interface includes the first interface pin and the second interface pin, and the first interface pin and the second interface pin can be one same pin or separate different pins.

15 Claims, 3 Drawing Sheets

INTERFACE CONTROL CIRCUIT AND CONTROL METHOD THEREOF

CROSS REFERENCE

The present invention claims priority to China 201710160096.1, filed on Mar. 17, 2017.

BACKGROUND OF THE INVENTION

Field of Invention

The present invention relates to an interface control circuit; particularly, it relates to an interface control circuit which can detect water by sensing a capacitance on a contact pin thereof. The present invention also relates to an interface control method.

Description of Related Art

FIG. 1 shows a prior art interface control circuit (interface control circuit 19) which may be for example but not limited to a USB Type C (Universal Serial Bus Type C) compliant interface control circuit. The interface control circuit 19 is for use in for example but not limited to data communication and/or power transmission with another compatible interface control circuit through contact pins of an interface connector 20 (for example but not limited to VBUS, CC1, CC2, D+ or D− as shown in the figure). However, the prior art interface circuit 19 has a problem that when the interface connector 20 contacts an electrolytic substance 30 (especially liquid, for example but not limited to water), either intentionally (such as taking a photos in the water or using a device when swimming) or unintentionally (such as inadvertently soaking in water, getting wet in the rain, or being splashed by drinks), the rusting process of the contact pins may be expedited due to electrolysis effect. Furthermore, under some circumstances, when the interface pin CC1 and/or CC2 (the interface control circuit 19 providing current sources through these pins) and VBUS (the interface control circuit 19 providing a voltage source through this pin) are functioning with water at the same time as shown in FIG. 1, a serious damage may happen.

Compared to the prior art shown in FIG. 1, the present invention has an advantage that it can detect the existence of an electrolytic substance, and execute corresponding protection operations when the electrolytic substance exists and is coupled to the interface pins (for example but not limited to pins VBUS, CC1, CC2, D+ or D− as shown in the figure), which can effectively slow down the rusting process so as to lengthen the product lifespan and protect the interface circuit and the interface connector.

SUMMARY OF THE INVENTION

From one perspective, the present invention generates an interface control circuit comprising: an interface transceiver circuit, coupled to an interface which includes at least one interface pin, and configured to operably transmit and/or receive an interface signal through the interface; and a protection circuit, configured to operably generate a protection control signal according to a contact pin capacitance of a first interface pin, wherein within a predetermined detection time period starting from when a second interface pin determines that an attaching event occurs, the protection circuit senses the contact pin capacitance of the first interface pin, and determines whether an electrolytic substance exists and is coupled to the first interface pin according to whether the contact pin capacitance is larger than a predetermined first capacitance threshold, and the protection control signal triggers the interface signal transceiver circuit to execute a protection operation when the electrolytic substance exists and is coupled to the first interface pin, wherein the interface includes the first interface pin and the second interface pin, wherein the first interface pin and the second interface pin are one same interface pin or separate different interface pins.

In one embodiment, the protection circuit includes: an electrolytic substance sensing circuit, including one of the following combinations: (1) a capacitance sensing resistor; and a charging switch, wherein the capacitance sensing resistor and the charging switch are electrically coupled in series between the first interface pin and a pull-up voltage, whereby a contact pin capacitance sensing signal is generated at the first interface pin, wherein the charging switch is turned on when the attaching event occurs; or (2) a charging current source; and a charging switch, wherein the charging current source and the charging switch are electrically coupled in series between the first interface pin and a pull-up voltage, whereby a contact pin capacitance sensing signal is generated at the first interface pin, wherein the charging switch is turned on when the attaching event occurs; and a determination circuit, configured to operably generate the protection control signal according to a comparison result generated by comparing the contact pin capacitance sensing signal to a reference voltage, wherein the reference voltage corresponds to the predetermined first capacitance threshold.

In one embodiment, the electrolytic substance sensing circuit further includes a discharging switch which is coupled to the first interface pin and is configured to operably discharge the contact pin capacitance sensing signal before the charging switch is turned on.

In one embodiment, the electrolytic substance has a dielectric constant which is larger than that of air or vacuum.

In one embodiment, the electrolytic substance includes water.

In one embodiment, the interface control circuit is compliant to an interface specification, the contact pin capacitance of the first interface pin being required to be smaller than a predetermined second capacitance threshold according to the interface specification, wherein the predetermined first capacitance threshold is larger than the predetermined second capacitance threshold.

In one embodiment, the interface pin is a USB Type C compliant connector pin.

In one embodiment, the first interface pin is a D+ or D− pin, and the second interface pin is a CC1 or CC2 pin according to USB Type C specification.

In one embodiment, the predetermined detection time period relates to a product of the resistance of the capacitance sensing resistor and/or the parasitic resistor multiplied by the predetermined first capacitance threshold.

From another perspective, the present invention provides a control method for controlling an interface control circuit which includes an interface transceiver circuit coupled to an interface which includes at least one interface pin, the interface transceiver being configured to operably transmit and/or receive an interface signal through the interface; the control method comprising: generating a protection control signal according to a contact pin capacitance of a first interface pin, wherein the step of generating the protection control signal includes: within a predetermined detection time period starting from when a second interface pin determines that an attaching event occurs, sensing the contact pin capacitance of the first interface pin; and determining whether an electrolytic substance exists and is coupled to the first interface pin according to whether the contact pin capacitance is larger than a predetermined first capacitance threshold; and triggering the interface signal transceiver circuit to execute a protection operation when the protection control signal indicates that the electrolytic substance exists and is coupled to the first interface pin; wherein the interface includes the first interface pin and the second interface pin, wherein the first interface pin and the second interface pin are one same interface pin or separate different interface pins.

The objectives, technical details, features, and effects of the present invention will be better understood with regard to the detailed description of the embodiments below.

DESCRIPTION OF THE PREFERRED EMBODIMENTS

The drawings as referred to throughout the description of the present invention are for illustration only, to show the interrelations between the circuits and the signal waveforms, but not drawn according to actual scale.

Figure 1:
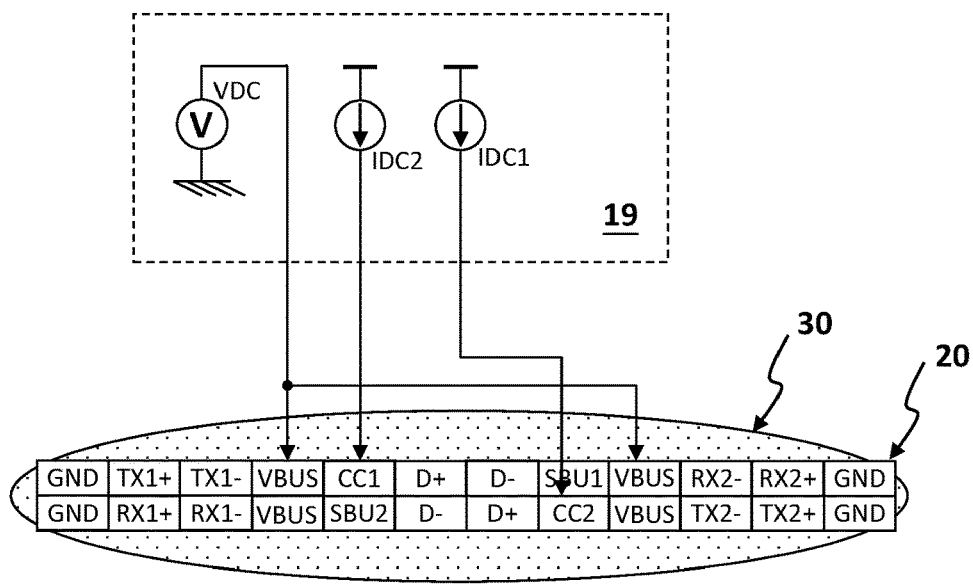
FIG. 1 shows a schematic diagram of a prior art interface control circuit.
Figure 2:
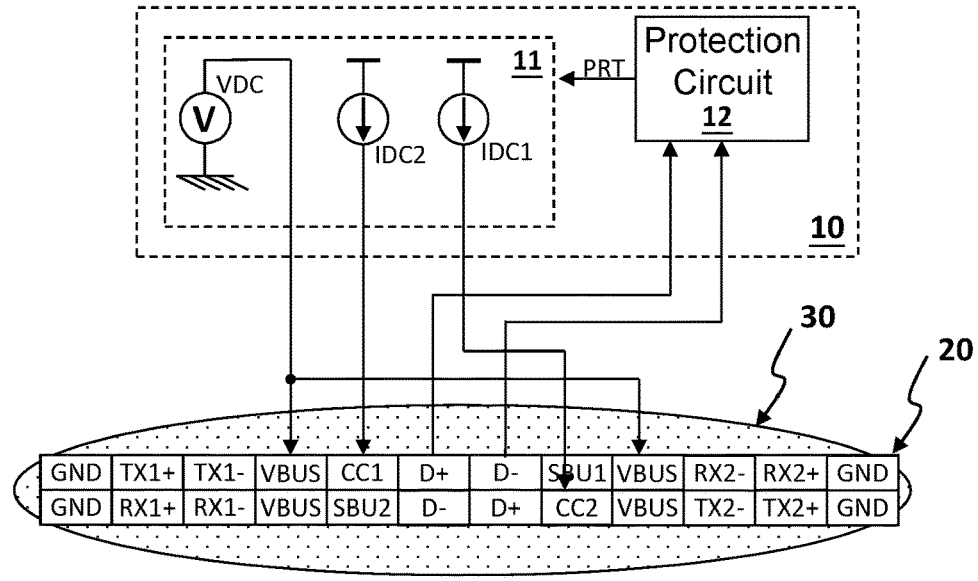
FIG. 2 shows a schematic diagram of one embodiment of the interface control circuit according to the present invention.

FIG. 2 shows a schematic diagram of one embodiment of the interface control circuit according to the present invention (interface control circuit 10). The interface control circuit 10 is for use in for example but not limited to data communication and/or power transmission with another interface control circuit (the interface control circuit 10 and the another interface control circuit for example are compliant to USB Type C specification as shown in the figure) through contact pins of an interface connector 20 (for example but not limited to pins VBUS, CC1, CC2, D+ or D− as shown in the figure). The interface control circuit 10 comprises an interface transceiver circuit 11 and a protection circuit 12. The interface transceiver circuit 11 is coupled to an interface (for example but not limited to USB PD) which includes at least one interface pin (for example but not limited to VBUS, CC1, CC2, D+ or D− as shown in the figure), and is configured to operably transmit and/or receive an interface signal through the interface, wherein the interface signal may be for example but not limited to a power or an analog or a digital signal. As an example, as shown in FIG. 2, the interface transceiver circuit 11 includes current sources IDC1 and IDC2 which are electrically connected with the interface pin CC1 and CC2 of the interface connector 20 respectively. And the interface transceiver circuit 11 also includes a voltage source VDC which is electrically connected with several interface pins VBUS of the connector 20.

The contact pin capacitance of at least some interface pins are strictly specified for achieving the highspeed data transmission requirement of the USB Type C interface. As an example, the equivalent contact pin capacitance of the interface pins D+ and D− relative to ground node GND should be less than 10 pF. On the other hand, the dielectric constant of an electrolytic substance such as water is generally far larger than that of air or vacuum, and therefore the equivalent contact pin capacitance of the interface pin D+ or D− will be much larger than the aforementioned specification (for example as high as several uF) when the interface pin D+ or D− contacts an electrolytic substance such as water. Hence, the protection circuit 12 can determine whether or not there is an electrolytic 30 existing and coupled to the interface pin D+ or D− according to the contact pin capacitance of the interface pin D+ or D−. In one embodiment, when the electrolytic 30 exists and is coupled to the interface pin D+ or D−, the protection circuit 12 can further generate a protection control signal PRT according to the contact pin capacitance of the interface pin D+ or D−, to trigger the interface transceiver circuit 11 to execute a protection operation.

In this embodiment, the aforementioned "contact pin capacitance" is an equivalent capacitance between an interface pin and any node (for example but not limited to an equivalent capacitance between the interface pin D+ or D− and the ground pin GND, or between the interface pin D+ or D− and a node which is or is not an interface pin). And the aforementioned "protection operation" may be for example but not limited to: shutting down a power, disabling other interface signals or other internal or external signals or circuits, to control the above to be non-conductive, to raise their output impedance, or to lower their output voltage or current, etc. In this embodiment, the aforementioned protection operations can be applied to for example but not limited to the pins VBUS, CC1, CC2, D+ or D−. As an example, VBUS can be controlled to stop generating its output voltage.

In one embodiment, within a predetermined detection time period starting from when an attaching event occurs on the interface pin CC1 or CC2 (the "attaching event" will be explained in more detail later), the protection circuit 12 can sense the contact pin capacitance of the interface pin D+ or D−, and determines that an electrolytic substance (e.g. water) exists and is coupled to the interface pin D+ or D− when the contact pin capacitance is larger than a predetermined capacitance threshold CTH. In one embodiment, the interface signal transceiver circuit 11 may be triggered to execute the aforementioned protection operation by the protection control signal PRT.

Note that the interface pin for use in detecting the existence of the electrolytic substance is not limited to the interface pin D+ or D−. According to the spirit of the present invention, any interface pin which has a normal contact pin capacitance or a specification-defined capacitance limit, and its capacitance when contacting an electrolytic substance will be larger than the normal contact pin capacitance or the specification-defined capacitance limit, can be used for the aforementioned detection.

The aforementioned "attaching event" means that an external object (circuit, wire, or substance) is in contact with one or more of the pins. For example, according to the USB Type C specification, by detecting for example but not limited to a change of the resistance or voltage of the interface pin CC1 and/or CC2 (for example by providing a current from the aforementioned current source IDC1 or IDC2), it can be determined as to whether or not a corresponding interface device is in connection with the interface connector 20. That is, according to the USB Type C specification, a change of the resistance or voltage of the interface pin CC1 and/or CC2 is one way to determine whether an "attaching event" occurs; however, the present invention is not limited to this. Any way which can determine whether there is an external object in contact with one or more of the pins can be used to determine whether an "attaching event" occurs. And, when the interface pin CC1 or CC2 contacts an electrolytic substance such as water, the resistance or voltage of the interface pin CC1 or CC2 also changes; therefore, although this "attaching event" is not a normal connection with another circuit or wire, it can still be found out and such an event can be used as a reference starting time point for sensing the contact pin capacitance.

In the aforementioned embodiments, the interface pin for determining the "attaching event" (i.e. CC1 or CC2) and the interface pin for sensing the contact pin capacitance (i.e. D+ or D−) are separate different pins. In another embodiment, the interface pin for determining the "attaching event" and the interface pin for sensing the contact pin capacitance can be one same interface pin.

Figure 3A:
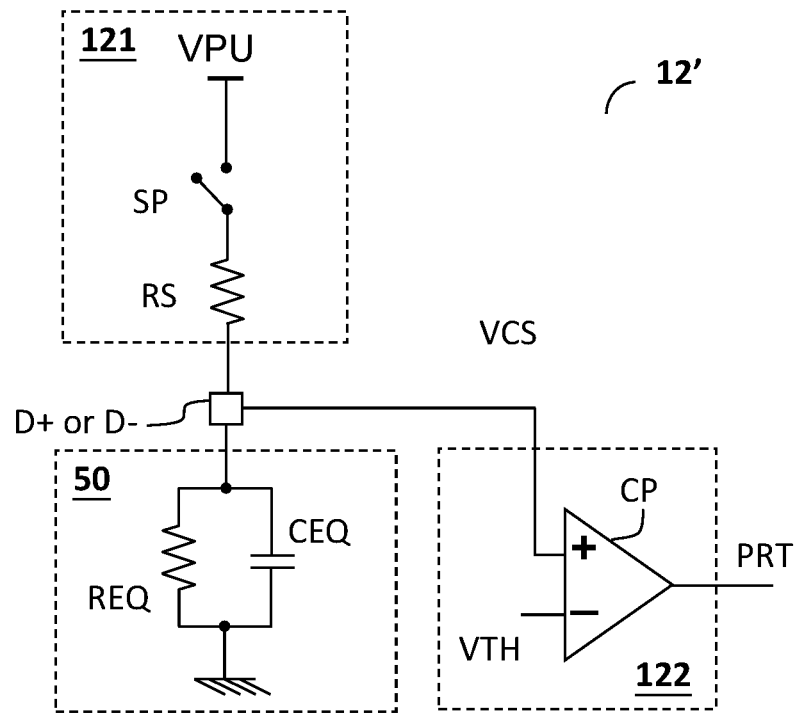
FIG. 3A shows a schematic diagram of one embodiment of the protection circuit of the interface control circuit according to the present invention.
Figure 4:
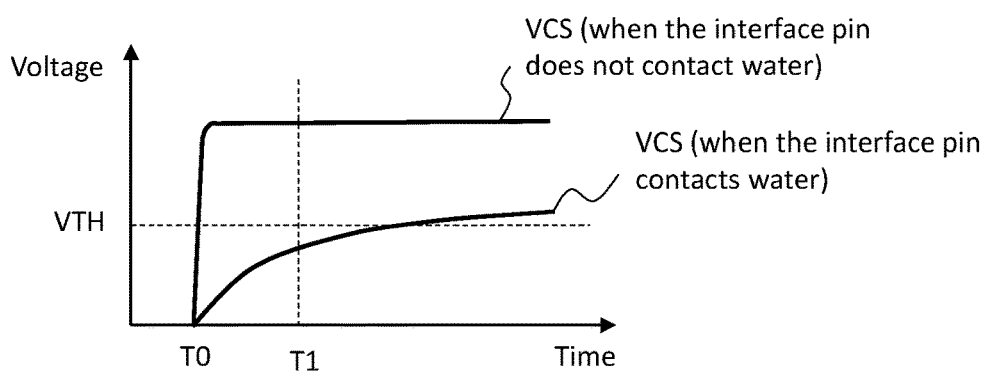
FIG. 4 shows schematic waveforms corresponding to FIGS. 3A-3C.

Please refer to FIGS. 3A and 4, wherein FIG. 3A shows a schematic diagram of one embodiment of the protection circuit (protection circuit 12') of the interface control circuit according to the present invention, and FIG. 4 shows schematic waveforms corresponding to FIG. 3A. As shown in FIG. 3A, the protection circuit 12' includes an electrolytic substance sensing circuit 121 and a determination circuit 122. The electrolytic substance sensing circuit 121 includes a capacitance sensing resistor RS and a charging switch SP, wherein the capacitance sensing resistor RS and the charging switch SP are electrically coupled in series between the interface pin D+ or D− and a pull-up voltage VPU, whereby a contact pin capacitance sensing signal VCS is generated at the interface pin D+ or D−.

More specifically, as shown in FIG. 3, as an equivalent circuit model of an electrolytic substance such as water, the equivalent circuit of electrolytic substance 50 includes an equivalent capacitor CEQ (corresponding to the contact pin capacitance) and an equivalent resistor REQ (corresponding to a parasitic resistor of the electrolytic substance 50). The charging switch SP is turned on when an attaching event occurs (for example at time point T0 as shown in FIG. 4). At this moment, the contact pin capacitance sensing signal VCS starts rising since the equivalent capacitor CEQ starts being charged. The time constant of the charging waveform is related to the resistance of the capacitance sensing resistor RS, the resistance of the equivalent resistor REQ, and the contact pin capacitance of the interface pin D+ or D−. The determination circuit 122 generates the protection control signal PRT according to a comparison result which is obtained by comparing the contact pin capacitance sensing signal VCS to a reference voltage VTH, wherein the reference voltage VTH corresponds to the aforementioned predetermined capacitance threshold CTH. In one embodiment, the determination circuit 122 may include a comparator circuit CP configured to operably compare the contact pin capacitance sensing signal VCS and the reference voltage VTH. More specifically, at a time point within a predetermined detection time period (for example at time point T1 as shown in FIG. 4) starting from the occurrence of the attaching event (T0), the determination circuit 122 can determine whether the contact pin capacitance of the interface pin D+ or D− is larger than the predetermined capacitance threshold CTH according to the comparison result (by reading or latching the comparison result), so as to determine whether an electrolytic substance exists and is coupled to the interface pin D+ or D−; the determination result for example can be expressed by a state of the protection control signal PRT. In the example shown in the figure, if the contact pin capacitance sensing signal VCS is smaller than the reference voltage VTH at time point T1, it means that the contact pin capacitance of the interface pin D+ or D− is larger than the predetermined capacitance threshold CTH, which indicates that an electrolytic substance exists and is coupled to the interface pin D+ or D−.

In one embodiment, the aforementioned reference voltage VTH relates to the pull-up voltage VPU. And in one embodiment, the aforementioned detection time period relates to a product of the resistance of the capacitance sensing resistor RS and/or the parasitic resistor of the electrolytic substance multiplied by the capacitance threshold CTH.

Figure 3B:
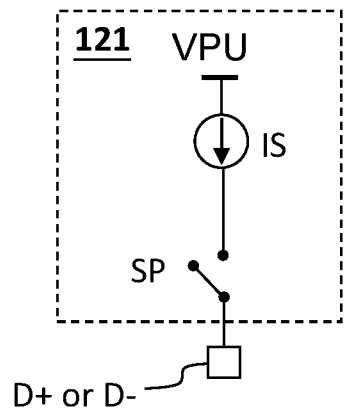
FIGS. 3B-3C show schematic diagrams of one embodiment of the electrolytic substance sensing circuit of the interface control circuit according to the present invention.

Please to FIG. 3B which shows a schematic diagram of one embodiment of the electrolytic substance sensing circuit (electrolytic substance sensing circuit 121) of the interface control circuit according to the present invention. In this embodiment, the electrolytic substance sensing circuit 121 includes a charging current source IS and a charging switch SP. The charging current source IS and the charging switch SP are electrically coupled in series between the interface pin D+ or D− and a pull-up voltage VPU, whereby a contact pin capacitance sensing signal VCS is generated at the interface pin D+ or D−, wherein the charging switch SP is turned on when the attaching event occurs.

Figure 3C:
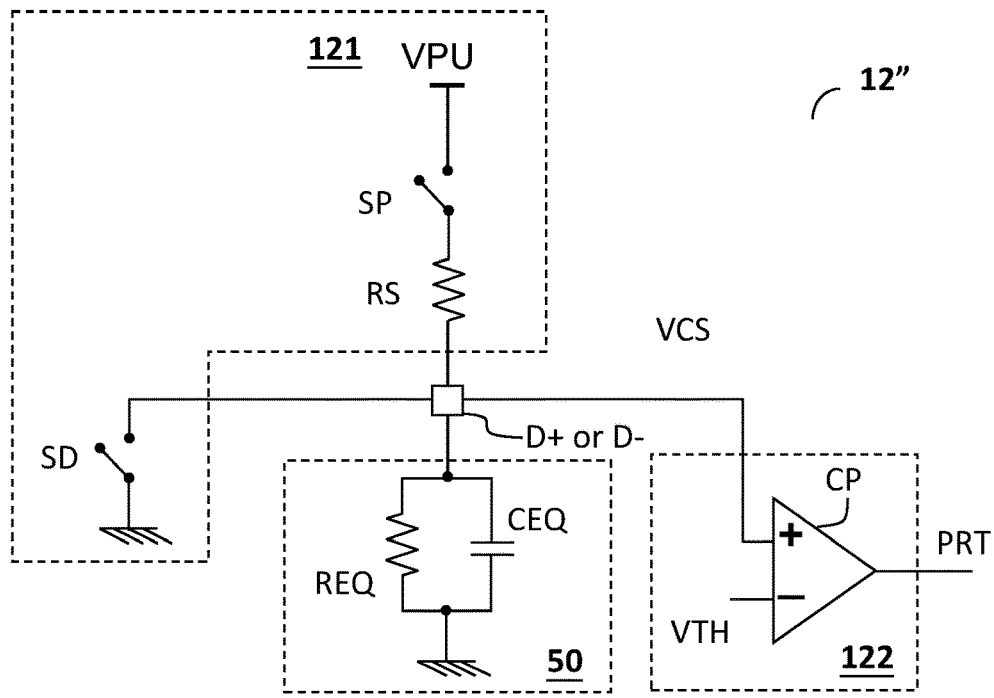
Figure 3D:
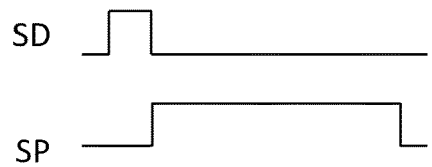
FIG. 3D shows a schematic waveform corresponding to the embodiment shown in FIG. 3C.

Please refer to FIG. 3C which shows a schematic diagram of one embodiment of the protection circuit (protection circuit 12") of the interface control circuit according to the present invention. As shown in the figure, in one embodiment, the electrolytic substance sensing circuit 121 further includes a discharging switch SD which is coupled to the interface pin D+ or D−. Referring to FIG. 3D also, the discharging switch SD is configured to operably discharge the contact pin capacitance sensing signal VCS before the charging switch is turned on. More specifically, in one preferred embodiment, electrolytic substance sensing circuit 121 starts to discharge the contact pin capacitance sensing signal VCS by the discharging switch SD when the attaching event occurs and starts to charge the contact pin capacitance sensing signal VCS after the contact pin capacitance sensing signal VCS is discharged to a certain level (for example to a ground level).

The present invention has been described in considerable detail with reference to certain preferred embodiments thereof. It should be understood that the description is for illustrative purpose, not for limiting the scope of the present invention. It is not limited for each of the embodiments described hereinbefore to be used alone; under the spirit of the present invention, two or more of the embodiments described hereinbefore can be used in combination. For example, two or more of the embodiments can be used together, or, a part of one embodiment can be used to replace a corresponding part of another embodiment. For example, in the aforementioned embodiments, the capacitance sensing resistor RS is coupled in series with the contact pin capacitor of the interface pin D+ or D−; however, the capacitance sensing resistor RS can be coupled in parallel with the contact pin capacitor, which can also achieve the same function of sensing the contact pin capacitance. As another example, to sense the contact pin capacitance, an AC signal can be applied instead of a DC signal. Furthermore, those skilled in this art can readily conceive variations and modifications within the spirit of the present invention. For example, to perform an action "according to" a certain signal as described in the context of the present invention is not limited to performing an action strictly according to the signal itself, but can be performing an action according to a converted form or a scaled-up or down form of the signal, i.e., the signal can be processed by a voltage-to-current conversion, a current-to-voltage conversion, and/or a ratio conversion, etc. before an action is performed. The spirit of the present invention should cover all such and other modifications and variations, which should be interpreted to fall within the scope of the following claims and their equivalents.

What is claimed is:

1. An interface control circuit, comprising:
   an interface transceiver circuit, coupled to an interface which includes at least one interface pin, and configured to operably transmit and/or receive an interface signal through the interface; and
   a protection circuit, configured to operably generate a protection control signal according to a contact pin capacitance of a first interface pin, wherein within a predetermined detection time period starting from when a second interface pin determines that an attaching event occurs, the protection circuit senses the contact pin capacitance of the first interface pin, and determines whether an electrolytic substance exists and is coupled to the first interface pin according to whether the contact pin capacitance is larger than a predetermined first capacitance threshold, and the protection control signal triggers the interface signal transceiver circuit to execute a protection operation when the electrolytic substance exists and is coupled to the first interface pin,
   wherein the interface includes the first interface pin and the second interface pin, wherein the first interface pin and the second interface pin are one same interface pin or separate different interface pins.

2. The interface control circuit of claim 1, wherein the protection circuit includes:
   an electrolytic substance sensing circuit, including one of the following combinations:
   (1) a capacitance sensing resistor; and
      a charging switch, wherein the capacitance sensing resistor and the charging switch are electrically coupled in series between the first interface pin and a pull-up voltage, whereby a contact pin capacitance sensing signal is generated at the first interface pin, wherein the charging switch is turned on when the attaching event occurs; or
   (2) a charging current source; and
      a charging switch, wherein the charging current source and the charging switch are electrically coupled in series between the first interface pin and a pull-up voltage, whereby a contact pin capacitance sensing signal is generated at the first interface pin, wherein the charging switch is turned on when the attaching event occurs; and
   a determination circuit, configured to operably generate the protection control signal according to a comparison result generated by comparing the contact pin capacitance sensing signal to a reference voltage, wherein the reference voltage corresponds to the predetermined first capacitance threshold.

3. The interface control circuit of claim 2, wherein the electrolytic substance sensing circuit further includes a discharging switch which is coupled to the first interface pin and is configured to operably discharge the contact pin capacitance sensing signal before the charging switch is turned on.

4. The interface control circuit of claim 1, wherein the electrolytic substance has a dielectric constant larger than that of air or vacuum.

5. The interface control circuit of claim 1, wherein the electrolytic substance includes water.

6. The interface control circuit of claim 1, wherein the interface control circuit is compliant to an interface specification, the contact pin capacitance of the first interface pin being required to be smaller than a predetermined second capacitance threshold according to the interface specification, wherein the predetermined first capacitance threshold is larger than the predetermined second capacitance threshold.

7. The interface control circuit of claim 1, wherein the interface pin is a USB Type C compliant connector pin.

8. The interface control circuit of claim 7, wherein the first interface pin is a D+ or D− pin, and the second interface pin is a CC1 or CC2 pin according to USB Type C specification.

9. The interface control circuit of claim 1, wherein the predetermined detection time period relates to a product of the resistance of the capacitance sensing resistor and/or the parasitic resistor multiplied by the predetermined first capacitance threshold.

10. A control method for controlling an interface control circuit which includes an interface transceiver circuit coupled to an interface which includes at least one interface pin, the interface transceiver being configured to operably transmit and/or receive an interface signal through the interface; the control method comprising:
    generating a protection control signal according to a contact pin capacitance of a first interface pin, wherein the step of generating the protection control signal includes:
       within a predetermined detection time period starting from when a second interface pin determines that an attaching event occurs, sensing the contact pin capacitance of the first interface pin; and
       determining whether an electrolytic substance exists and is coupled to the first interface pin according to whether the contact pin capacitance is larger than a predetermined first capacitance threshold; and
    triggering the interface signal transceiver circuit to execute a protection operation when the protection control signal indicates that the electrolytic substance exists and is coupled to the first interface pin;
    wherein the interface includes the first interface pin and the second interface pin, wherein the first interface pin and the second interface pin are one same interface pin or separate different interface pins.

11. The control method of claim 10, wherein the electrolytic substance has a dielectric constant larger than that of air or vacuum.

12. The control method of claim 10, wherein the electrolytic substance includes water.

13. The control method of claim 10, wherein the interface pin is a USB Type C compliant connector pin.

14. The control method of claim 10, wherein the first interface pin is a D+ or D− pin, and the second interface pin is a CC1 or CC2 pin according to USB Type C specification.

15. The control method of claim 10, wherein the predetermined detection time period relates to a product of the resistance of the capacitance sensing resistor and/or the parasitic resistor multiplied by the predetermined first capacitance threshold.

\* \* \* \* \*